United States Patent
Jain et al.

(10) Patent No.: US 9,877,964 B2
(45) Date of Patent: Jan. 30, 2018

(54) METHODS AND COMPOSITIONS FOR TREATING DRY EYE DISEASE AND OTHER EYE DISORDERS

(71) Applicants: The Board of Trustees of the University of Illinois, Urbana, IL (US); Ocugen, Inc., Malvern, PA (US)

(72) Inventors: Sandeep Jain, Oak Park, IL (US); Uday Bhaskar Kompella, Englewood, CO (US); Shankar Musunuri, Chester Springs, PA (US)

(73) Assignees: Ocugen, Inc., Malvern, PA (US); The Board of Trustees of the University of Illinois, Urbana, IL (US)

( * ) Notice: Subject to any disclaimer, the term of this patent is extended or adjusted under 35 U.S.C. 154(b) by 0 days.

(21) Appl. No.: 15/464,290

(22) Filed: Mar. 20, 2017

(65) Prior Publication Data

US 2017/0189396 A1    Jul. 6, 2017

Related U.S. Application Data

(63) Continuation-in-part of application No. 15/051,654, filed on Feb. 23, 2016, now Pat. No. 9,597,328.

(60) Provisional application No. 62/119,857, filed on Feb. 24, 2015.

(51) Int. Cl.
| | |
|---|---|
| *A61K 31/496* | (2006.01) |
| *A61K 31/498* | (2006.01) |
| *A61K 9/00* | (2006.01) |
| *A61K 9/08* | (2006.01) |
| *A61K 9/06* | (2006.01) |
| *A61K 47/02* | (2006.01) |
| *A61K 47/10* | (2017.01) |
| *A61K 47/12* | (2006.01) |
| *A61K 47/14* | (2017.01) |
| *A61K 47/18* | (2017.01) |
| *A61K 47/26* | (2006.01) |
| *A61K 47/32* | (2006.01) |
| *A61K 47/36* | (2006.01) |
| *A61K 9/107* | (2006.01) |
| *A61K 47/38* | (2006.01) |
| *A61K 31/573* | (2006.01) |

(52) U.S. Cl.
CPC .......... *A61K 31/498* (2013.01); *A61K 9/0048* (2013.01); *A61K 9/06* (2013.01); *A61K 9/08* (2013.01); *A61K 9/107* (2013.01); *A61K 31/573* (2013.01); *A61K 47/02* (2013.01); *A61K 47/10* (2013.01); *A61K 47/12* (2013.01); *A61K 47/14* (2013.01); *A61K 47/183* (2013.01); *A61K 47/26* (2013.01); *A61K 47/32* (2013.01); *A61K 47/36* (2013.01); *A61K 47/38* (2013.01)

(58) Field of Classification Search
None
See application file for complete search history.

(56) References Cited

U.S. PATENT DOCUMENTS

| | | |
|---|---|---|
| 8,575,207 B2 | 11/2013 | Gil et al. |
| 2005/0196370 A1 | 9/2005 | Yu et al. |
| 2008/0050335 A1 | 2/2008 | Faoue |
| 2014/0088199 A1 | 3/2014 | Sharma |

OTHER PUBLICATIONS

Cantor, Louis B., in "Brimonidine in the treatment of glaucoma and ocular hypertension", Therapeutics and Clinical Risk Management 2006:2(4) 337-346.
Office Action for U.S. Appl. No. 15/051,654, dated Sep. 26, 2016.

*Primary Examiner* — Robert A Wax
*Assistant Examiner* — Quanglong N Truong
(74) *Attorney, Agent, or Firm* — Don D. Cha; Hamilton DeSanctis & Cha, LLP

(57) ABSTRACT

The present invention relates to a method for treating a dry eye syndrome using an alpha 2 adrenergic agonist, pharmaceutically acceptable salt thereof or a mixture thereof. In particular, the alpha 2 adrenergic agonist of the invention has a higher alpha 2A agonist activity compared to alpha 2B agonist activity. This invention also relates to an ophthalmic composition comprising a therapeutically effective amount of an alpha 2 adrenergic agonist, a pharmaceutically acceptable salt thereof or a combination thereof as an active ingredient for treating a dry eye syndrome.

26 Claims, No Drawings

METHODS AND COMPOSITIONS FOR TREATING DRY EYE DISEASE AND OTHER EYE DISORDERS

CROSS-REFERENCE TO RELATED APPLICATIONS

This application is Continuation-In-Part of U.S. patent application Ser. No. 15/051,654 filed Feb. 23, 2016, which claims the priority benefit of U.S. Provisional Application No. 62/119,857 filed Feb. 24, 2015, which are incorporated herein by reference in their entirety.

FIELD OF THE INVENTION

The present invention relates to a pharmaceutical preparation for treatment of eye disorders containing an alpha 2 adrenergic agonist, to processes for producing the pharmaceutical preparation and methods for treatment of various eye disorders including dry eye and Meibomian gland dysfunction. In particular, the alpha 2 adrenergic agonist of the invention has a higher alpha 2A agonist activity compared to alpha 2B agonist activity. This invention also relates to a medicinal applicator for topical application of an alpha 2 adrenergic agonist to a subject, a package assembly for the medicinal applicator and methods of using the medicinal applicator to treat eye disorders including Meibomian gland dysfunction.

BACKGROUND OF THE INVENTION

The two major classes of dry eye (or dry eye syndrome) are aqueous tear-deficient dry eye (ADDE) and evaporative dry eye (EDE). There are also cases of mixed mechanism dry eye (i.e., both ADDE and EDE). ADDE is due to failure of lacrimal tear secretion and this class can be further subdivided into Sjogren syndrome dry eye (where the lacrimal and salivary glands are targeted by an autoimmune process, e.g., rheumatoid arthritis) and non-Sjogren's syndrome dry eye (lacrimal dysfunction, but the systemic autoimmune features of Sjogren's syndrome are excluded, e.g., age-related dry eye). EDE is due to excessive water loss from the exposed ocular surface in the presence of normal lacrimal secretory function. Its causes can be extrinsic (e.g., ocular surface disorder due to some extrinsic exposure, contact lens wear or vitamin A deficiency) or intrinsic (e.g., Meibomian gland dysfunction and disorders of eyelid aperture).

Meibomian glands, sebaceous glands in the tarsus of the eyelids, consist of multiple acini emptying into a central duct that opens at the surface of the lid margin just anterior to the mucocutaneous junction. The eyelid margin is for most part lined by the skin. The cornified skin-type epithelium of eyelid margin abruptly changes to non-keratinized epithelium posterior to the opening of the meibomian gland ducts (PMID: 21413985). Blood vessels and nerves are located in deeper layers of skin and in the substantia propria.

Meibomian glands secrete a mixture of lipids and other components that form the outer layer of the preocular tear film. This lipid layer functions to decrease tear film evaporation. Meibomian gland dysfunction (MGD) leads to evaporative dry eye disease. Typical slit lamp biomicroscope findings in MGD include: lid margin telangiectasia, anastomosis of vessels on mucocutaneous junction, poor expression of Meibomian secretions by digital pressure, turbid meibum with increased paste like consistency, dropout of Meibomian gland acini and obliteration of Meibomian duct orificies. One of the most well recognized clinic finding in MGD is the presence of numerous telangiectatic blood vessels coursing across the eyelid margin. MGD also accompanies tear deficient dry eye disease, like ocular Graft-versus-host-disease (oGVHD) and Sjogren's dry eye syndrome. Treatment of Meibomian gland dysfunction by topical application of therapeutic agents would therefore provide an attractive treatment of evaporative dry eye disease and mixed mechanism dry eye disease.

Dry eye symptoms have traditionally been managed with eyelid hygiene, topical antibiotics (erythromycin or bacitracin ointments), oral tetracyclines (tetracycline, doxycycline, or minocycline), anti-inflammatory compounds (cyclosporine) and corticosteroids which are often time consuming, frustrating, and frequently ineffective or variably effective treatments. Further, ointments, creams etc., may not disrupt the barriers including mucosal, mucocutaneous, and stratum corneal layers (superficial cornified layers of skin) and may not reach the blood vessels and nerves that are present deeper in the eyelid tissue. Thus, there exists an ongoing need for methods and compositions for enhancing the bioavailability of drugs in the vicinity of the target tissues (blood vessels and nerves). Furthermore, cyclosporine-A (Restasis®) is the only approved treatment for dry eye syndrome in U.S. but it is only indicated for part of the dry eye patients whose tear production is presumed to be suppressed due to ocular inflammation associated with keratoconjunctivitis sicca. Despite the high incidence of dry eye and other eye disorders, there is currently no consistently effective treatment for these conditions and it still remains a therapeutic challenge. As such, there is a need for new therapeutic modalities to treat eye disorders including MGD and dry eye syndrome.

SUMMARY OF THE INVENTION

Some aspects of the invention are based on surprising and unexpected discovery by the present inventors that α-2 adrenergic agonist can be used to treat dry eye syndrome. Conventional methods of treating a dry eye syndrome typically use an oil or hyaluronic acid. These solutions only relieve symptoms of dry eye syndrome but do not treat the underlying cause In contrast, the active ingredient in treating dry eye syndrome using the method of the invention involves administering a therapeutically effective amount of an alpha 2 adrenergic agonist, a pharmaceutically acceptable salt thereof or a combination thereof. As used herein, the term "active ingredient" when reference to treating dry eye syndrome refers to a compound that is responsible for treating a dry eye syndrome. A wide variety of ophthalmic solutions contain an alpha 2 adrenergic agonist. However, none of the conventional ophthalmic solutions use alpha 2 adrenergic agonist to treat a dry eye syndrome. In fact, prior to discovery by the present inventors, no one has even recognized an alpha 2 adrenergic agonist is effective in treating a dry eye syndrome.

In some embodiments, the ophthalmic solution of the invention for treating a dry eye syndrome consists essentially of an alpha 2 adrenergic agonist as the active ingredient and optionally one or more of the following components a pharmaceutically acceptable excipient; and water. Still in other embodiments, the alpha 2 adrenergic agonist or a pharmaceutically acceptable salt thereof used in treating a

DETAILED DESCRIPTION OF THE INVENTION

This invention provides ophthalmic formulations containing an alpha 2 adrenergic agonist for the treatment of eye disorders including Meibomian gland dysfunction (MGD) and dry eye syndrome. In particular, the active compound for treating a dry eye syndrome consists essentially of alpha 2 adrenergic agonist. In some embodiments, the active compound consists of alpha 2 adrenergic agonist having a higher alpha 2A agonist activity compared to alpha 2B agonist activity.

Representative alpha 2 adrenergic receptor agonist include 4-NEMD, 7-Me-marsanidine, Agmatine, Apraclonidine, Brimonidine, Cannabigerol, Clonidine, Detomidine, Dexmedetomidine, Fadolmidine, Guanabenz, Guanfacine, Lofexidine, Marsanidine, Medetomidine, Methamphetamine, Mivazerol, Rilmenidine, Romifidine, Talipexole, Tizanidine, Tolonidine, Xylazine, Xylometazoline, and the like including pharmaceutically acceptable salts thereof. In one particular embodiment, the alpha 2 adrenergic receptor agonist is brimonidine (5-Bromo-N-(4,5-dihydro-1H-imidazol-2-yl) quinoxalin-6-amine), a pharmaceutically acceptable salt thereof or a combination thereof.

In some embodiments, the alpha 2 adrenergic agonist used in ophthalmic compositions of the invention has a higher alpha 2A agonist activity compared to alpha 2B agonist activity. In some instances, the alpha 2A agonist activity of the alpha 2 adrenergic agonist is at least about 10% greater, typically at least about 20% greater and often at least about 30% greater than its alpha 2B agonist activity. As used herein, the term "about" when referring to a numeric value means ±20%, typically ±10%, often ±5% and most often ±2% of the numeric value.

In other embodiments, the alpha 2 adrenergic receptor agonist may be applied alone or in combination with non-alpha 2 adrenergic receptor agonist agents such as corticosteroids (e.g., methylprednisolone, hydrocortisone, betamethasone and dexamethasone), CRGP receptor antagonists or anti-CGRP receptor monoclonal antibodies. Other combinations can include inhibitors of adrenomedullin, serotonin, cathelicidin and neuropeptides such as NPY.

In an embodiment, the composition comprises about 0.001 to about 5 mg/ml Brimonidine in aqueous medium. In another embodiment, the composition comprises about 0.15 mg/ml Brimonidine in aqueous solution. A particular composition comprises about 0.15 mg/ml Brimonidine and about 0.5 mg/ml Methylprednisone in aqueous solution.

Optionally, an amount of a penetrating agent may also be included in any of the compositions of the invention to aid penetration of the active component into and across the skin or eyelid skin such as for example, aliphatic alcohol, fatty acid and a salt thereof, fatty acid ester, polyalcohol alkyl ether, polyoxyethylene alkyl ether, glyceride, polyalcohol medium chain fatty acid ester, polyoxyethylene sorbitan fatty acid ester, alkyl lactate ester, terpenes and organic amine. More specifically, the percutaeous penetrating agent may be ethanol, glycerol, diethylene glycol, propylene glycol, polyethylene glycol and higher aliphatic alcohols (saturated or unsaturated higher aliphatic alcohol having 12 to 22 carbon atoms such as oleyl alcohol, lauryl alcohol and stearyl alcohol), capric acid, myristic acid, palmitic acid, lauric acid, stearic acid, isostearic acid, oleic acid, linoleic acid and linolenic acid, and a salt thereof (for example, sodium salt, potassium salt, magnesium salt, calcium salt and aluminium salt), include an ester of a fatty acid such as myristic acid, palmitic acid, lauric acid, stearic acid, isostearic acid, oleic acid, linoleic acid, linolenic acid, propionic acid, butyric acid, isobutyric acid, valeric acid, pivalic acid, caproic acid, heptanoic acid, malonic acid, succinic acid, glutaric acid, adipic acid, pimelic acid, crotonic acid, sorbic acid, maleic acid, fumaric acid and sebacic acid with a lower aliphatic alcohol such as methanol, ethanol, propanol, isopropanol, butanol, pentanol, hexanol, heptanol and octanol, isopropyl myristate, isopropyl palmitate, diisopropyl adipate and diethyl sebacate, an ether of a polyalcohol such as glycerol, ethylene glycol, propylene glycol, 1,3-butylene glycol, diglycerol, polyglycerol, diethylene glycol, polyethylene glycol, dipropylene glycol, polypropylene glycol, sorbitan, sorbitol, methyl glucoside, oligosaccharide and reduced oligosaccharide with alkyl alcohol, polyoxyethylene lauryl ether, polyoxyethylene cetyl ether, polyoxyethylene stearyl ether and polyoxyethylene oleyl ether, glycerol ester of fatty acid having 6 to 18 carbon atoms (e.g:, monoglyceride, diglyceride, triglyceride and a mixture thereof), glyceryl monolaurate, glyceryl monomyristate, glyceryl monostearate, glyceryl monooleate, glyceryl dilaurate, glyceryl dimyristate, glyceryl distearate, glyceryl trilaurate, glyceryl trimyristate and glyceryl tristearate, ethylene glycol monocaprylate, propylene glycol monocaprylate, glycerin monocaprylate, mono 2-ethylene glycol ethylhexanoate, mono 2-propylene glycol ethylhexanoate, di(2-propylene)glycol ethylhexanoate, propylene glycol, dicaprylate, polyoxyethylene sorbitan monolaurate, polyoxyethylene sorbitan monostearate and polyoxyethylene sorbitan monooleate, methyl lactate, ethyl lactate, methyl 2-methoxy propionate and ethyl 2-methoxypropionate, monoethanolamine, triethanolamine, creatinine and meglumine. In certain embodiments of the invention one or more of fatty acid ester, polyoxyethylene, isopropyl myristate and polyoxyethylene oleyl ether is included in the composition. In other embodiments of the invention a penetrating agent or combination of agents such as 1-acyl-azacyclohepan-2-one (azone), 1-acyl-glucoside, 1-acyl- poly(oxyethylene), 1-acyl-saccharide, 2-(n-acyl)-cyclohexanone, 1-alkanol, 1-alkanoic acid, 2-(n-acyl)-1,3-doxolane (SEP A), 1,2,3-triacylglyceride, 1-alkylacetate, alkyl-sulfate, dialkyl sulfate, and phenyl-alkyl-amine may be added to the composition.

Also optionally, an amount of a hydrating agent such as hyaluronic acid, saline solution, and/or polyvinylpyrrolidone, may be included in any of the compositions of the invention. Ophthalmic compositions of the invention that are intended to penetrate the barriers generally, although not necessarily, include an amount of a hydrating agent to facilitate penetration of the therapeutic agent through the cell or junctions of the barriers including mucosal, mucocutaneous, and stratum corneum layers.

When included in the compositions of the invention, penetrating agents are generally in the amount of from 0.01% to 50% by weight of the composition and in some embodiments from 0.1% to about 40% by weight of the composition, 1% to about 35% and in other embodiments from about 5% to about 30% by weight of the composition and the amount of hydrating agent is in the range of from 0.001% to 30% by weight of the composition, in other embodiments from 0.01 to 25% by weight of the composition and in still other embodiments, from 0.1% to 10% by weight of the composition.

In addition to the components discussed above, any component generally used for manufacturing medicine in the desired form can be added to the present compositions of the invention, if desired. Examples of such components include a base matrix for adhesive preparations, an ointment base, gel base, solvent, oil, crosslinking agent, surfactant, gum, resin, pH adjuster, stabilizer, antioxidant, preservative, ultraviolet absorbent and wetting agent. A percutaneous absorption enhancer can be added, if desired.

Surfactant may be included in the compositions of the invention to facilitate dissolution of formulation components and/or absorption, including anionic surfactant, cationic surfactant, nonionic surfactant and amphoteric surfactant. Useful surfactants include fatty acid salt, alkyl sulfate, polyoxyethylene alkyl sulfate, alkyl sulfo carboxylate, alkyl ether carboxylate, amine salt, quanternary ammonium salt, polysorbate 80, poloxamers, polyoxyethylene hydrogenated castor oil, polyoxyethylene fatty acid ester, polyoxyethylene alkyl ether, polyoxyethylene sorbitan fatty acid ester, alkyl betaine, dimethylalkylglycine and lecithin.

If desired, gum and/or resin may be included in the compositions of the invention, including for example, sodium polyacrylate, cellulose ether, calcium alginate, carboxyvinyl polymer, ethylene-acrylic acid copolymer, vinyl pyrrolidone polymer, vinyl alcohol-vinyl pyrrolidone copolymer, nitrogen-substituted acrylamide polymer, polyacrylamide, cationic polymer such as cationic guar gum, dimethylacrylic ammonium polymer, acrylic acid-methacrylic acid copolymer, polyoxyethylene-polypropylene copolymer, polyvinyl alcohol, pullulan, agar, gelatine, chitosan, polysaccharide from tamarindo seed, xanthan gum, caragenean, high-methoxyl pectin, low-methoxyl pectin, guar gum, acacia gum, microcrystalline cellulose, arabinogalactan, karaya gum, tragacanth gum, alginate, albumin, casein, curdlan, gellan gum, dextran, cellulose, polyethyleneimine, high polymerized polyethylene glycol, cationic silicone polymer, synthetic latex, acrylic silicone, trimethylsiloxysilicate and fluorinated silicone resin.

A pH adjuster may be used in the compositions to adjust pH of the composition to a desired range, such as pH 4-10, or pH 5-8, for example or any range that maximizes the penetration through the skin of the particular drug in the composition. pH adjustment can be achieved through use of various chemicals such as hydrochloric acid, citric acid, sodium citrate, acetic acid, sodium acetate, ammonium acetate, succinic acid, tartaric acid, L-sodium tartrate, sodium hydrate, potassium hydrate, sodium carbonate, sodium hydrogencarbonate, lactic acid, calcium lactate, sodium lactate, sodium fumarate, sodium propionate, boric acid, ammonium borate, maleic acid, phosphoric acid, sodium hydrogenphosphate, dl-malic acid, adipic acid, triethanolamine, diisopropanolamine, meglumine, monoethanolamine, sulfuric acid and aluminum potassium sulfate and the like.

Stabilizers may optionally be included in the compositions of the invention. Useful stabilizers include for example sodium bisulfate, sodium sulfite, sodium pyrosulfite, sodium formaldehyde sulfoxylate, L-ascorbic acid, erythorbic acid, L-cysteine, thioglycerol, butylated hydroxyanisole (BHA), butylated hydroxytoluene (BHT), propyl gallate, ascorbyl palmitate, dl-α-tocopherol, nordihydroguaiaretic acid, 1-hydroxyethylidene-1,1-diphosphonic acid, disodium edetate, tetrasodium edetate dehydrate, sodium citrate, sodium polyphosphate, sodium metaphosphate, gluconic acid, phosphoric acid, citric acid, ascorbic acid and/or succinic acid.

Other optional components of the compositions include wetting agents such as glycerol, polyethylene glycol, sorbitol, mannitoltol, propylene-glycol, 1,3-butanediol and hydrogenated maltose syrup; antioxidants such as sodium bisulfate, sodium sulfite, sodium pyrosulfite, sodium formaldehyde sulfoxylate, L-ascorbic acid, erythorbic acid, L-cysteine, thioglycerol, butylated hydroxyanisole (BHA), butylated hydroxytoluene (BHT), propyl gallate, ascorbyl palmitate, dl-.alpha.-tocopherol and nordihydroguaiaretic acid; preservatives such as methylparaben, propylparaben, chlorobutanol, benzyl alcohol, phenylethyl alcohol, benzalkonium chloride, phenol, cresol, thimerosal, dehydroacetic acid and sorbic acid; ultraviolet absorbent such as octyl methoxycinnamate, glyceryl monooctanoate di-paramethoxy cinnamate, 2-hydroxy-4-methoxybenzophenone, para-aminobenzoic acid, para-aminobenzoic acid glycerol ester, N,N-dipropoxy-para-aminobenzoic acid ethyl ester, N,N-diethoxy-para-aminobenzoic acid ethyl ester, N,N-dimethyl-para-aminobenzoic aid ethyl ester, N,N-dimethyl-para-aminobenzoic acid butyl ester, homomethyl N-acetylanthranilate, amyl salicylate, menthyl salicylate, homomethyl salicylate, octyl salicylate, phenyl salicylate, benzyl salicylate and p-isopropyl phenyl salicylate.

The formulations are not limited in form and may include for example liposomes and other vesicles, such as transfersomes, which include surface active agents and are particularly useful for the transdermal delivery of large molecules such as peptide and proteins; and thosomes, which are liposomes that contain ethanol, which functions as a permeation enhancer.

In an embodiment, the liquid composition is prepared using a physiological saline solution as a major vehicle. The pH of such solutions should preferably be maintained between 4.5 and 8.0 with an appropriate buffer system, a neutral pH being preferred but not essential. The formulations may also contain conventional, pharmaceutically acceptable preservatives, stabilizers and surfactants. Preferred preservatives that may be used in the pharmaceutical compositions of the present invention include, but are not limited to, benzalkonium chloride, chlorobutanol, thimerosal, phenylmercuric acetate and phenylmercuric nitrate, polyquaternium-1 or mixtures of individual components. A preferred surfactant is, for example, Tween 80. Likewise, various preferred vehicles may be used in the ophthalmic preparations of the present invention. These vehicles include, but are not limited to, polyvinyl alcohol, povidone, hydroxypropyl methyl cellulose, poloxamers, carboxymethyl cellulose, hydroxyethyl cellulose cyclodextrin and purified water (water).

Tonicity adjustors may be added as needed or convenient. They include, but are not limited to, salts, particularly sodium chloride, potassium chloride, mannitol and glycerin, or any other suitable ophthalmically acceptable tonicity adjustor. Various buffers and means for adjusting pH may be used so long as the resulting preparation is ophthalmically acceptable. Accordingly, buffers include acetate buffers, citrate buffers, phosphate buffers and borate buffers. Acids or bases may be used to adjust the pH of these formulations as needed. In a similar vein, an ophthalmically acceptable antioxidant for use in the present invention includes, but is not limited to, sodium metabisulfite, sodium thiosulfate, acetylcysteine, butylated hydroxyanisole and butylated hydroxytoluene. Other excipient components which may be included in the ophthalmic preparations are chelating agents and antibiotics. The preferred chelating agent is edetate disodium, although other chelating agents may also be used in place of or in conjunction with it. Non-limiting examples of antibiotics useful in the present invention include trimethoprim sulfate/polymyxin B sulfate, gatifloxacin, moxifloxacin hydrochloride, tobramycin, teicoplanin, vancomycin, azithromycin, clarithromycin, amoxicillin, penicillin, ampicillin, carbenicillin, ciprofloxacin, levofloxacin, amikacin, gentamicin, kanamycin, neomycin and streptomycin, The ingredients are usually used in the following amounts: Ingredient Amount (% w/v) active ingredient about 0.001-5; preservative 0-0.10; vehicle 0-40; tonicity adjustor 0-10; buffer 0.01-10; pH adjustor q.s. pH 4.5-8.0; antioxidant as needed; surfactant as needed; and purified water as needed to make 100%.

Thus, in an aspect, the present invention generally relates to ophthalmological compositions or formulations having an alpha 2 adrenergic agonist and various components exemplified above (non-alpha 2 adrenergic agonist active agents e.g., corticosteriods and other active agents, a penetration enhancer, a hydrating agent, a surfactant, a gum, a resin, a pH adjuster, a stabilizer, a wetting agent and/or a tonicity adjustor) generally used for manufacturing a medicine, for example, in the form of a liquid, an emulsion, or a suspension, an ointment, a gel, an aerosol, a mist, a polymer, a film or a paste. The ophthalmological formulations containing water include dosage forms such as ophthalmic oil-in-water emulsions, eye hydrogels, eye drop solutions, eyebaths, eye lotions, eye inserts, eye ointments and eye sprays and preparations for intraocular application. These formulations of the present invention contain about 0.01 to about 5 mg/ml (about 0.001% to about 0.5%) preferably about 0.2% or less (e.g., 0.05-0.2% preferably 0.07-0.15%) of brimonidine or a salt thereof (e.g., brimonidine tartrate). The ingredient amounts are presented in units of either % weight/volume (% w/v) or weight/weight (% w/w).

To provide the ophthalmic formulations with a pH substantially corresponding to the pH of the fluids of the eye or at an acceptable physiological pH, as described above, the pH of the ophthalmic formulation can be adjusted, if required, by addition of an acid or a base. In this regard, the ophthalmic formulations have a pH value in the range of about 6.8 to about 8, preferably about 7.4 to about 8.0 or so that the pH of the ophthalmic formulation substantially corresponds to the pH value of the fluids in the human eye. To buffer the ophthalmic formulation at the desired pH, an effective amount of at least one buffer (also referred to herein as buffer component) can be incorporated into the formulation. The effective amount of buffer component employed to buffer or maintain or stabilize the formulation at the desired pH can vary and depends to a large degree on the particular buffer component employed, as well as the chemical composition of the ophthalmic formulation. When it is determined that the buffered ophthalmic formulation does not have the desired pH value, the pH of the aqueous buffered ophthalmic formulation can be adjusted by the addition of acids or bases in quantity sufficient to achieve the desired pH. An example of an acid which can be used to adjust the pH of the aqueous buffered ophthalmic formulation is IN hydrochloric acid and an example of a base which can be used to adjust the pH of the aqueous buffered ophthalmic formulation is 1N sodium hydroxide. In an embodiment of the invention, however, the ophthalmic formulations of the present invention contain a combination of dibasic and monobasic phosphate or boric acid and sodium borate—as buffering agents. The formulations contain an amount of boric acid and sodium borate sufficient to buffer the formulation in a pH range of 7.5-8.0 or dibasic and monobasic phosphate sufficient to buffer the formulation in a pH range of 7.5-8.0. In addition, boric acid and its ophthalmically acceptable acid addition salts, as well as borate-polyol complexes, known in the art, can contribute to preservative effectiveness.

The ophthalmic formulations can have an osmolality or tonicity of at least about 200 mOsmol/kg, preferably in the range of about 200 to about 350 or about 400 mOsmol/kg. In a preferred embodiment, the osmolality or tonicity of the formulation substantially corresponds to the tonicity of the fluids of the eye, in particular the human eye. In one embodiment, the tonicity adjustor is selected from inorganic salts such as sodium chloride, potassium chloride, calcium chloride and magnesium chloride and mixtures thereof.

Generally speaking, when ophthalmological formulations are applied topically in the form of, for example, drops or ointment to the cornea, the dosage form rapidly disperses into the tear film and flows into the tear drainage system, thereby reducing ocular bioavailability of the active ingredient. In practicing the present invention, one skilled in the art would be able to address such issues by adjusting the dosing regimens (e.g., once a day, two times per day or four times per day, etc.) and/or by the use of drug delivery systems such as soft contact lenses, collagen shields, scleral lenses, etc., as a means of increasing bioavailability of alpha 2 adrenergic agonist in the precorneal area and ocular surface, lid margins, cornea, and to the anterior chamber of the eye, as necessary to treat MGD or dry eye. Such delivery systems and their manufacture are known in the art.

The formulations of the present invention can be packaged in various package forms known in the field of topical ophthalmics. In one embodiment, the formulation is packaged in sterile, preservative-free single-use packs or vials or containers (i.e., the unit dose vials). Each vial, for example as small as a 0.9 mL, may be made of low density polyethylene so as to contain a small quantity of the formulation, e.g. 0.4 mL fill until use. This way, where the pharmaceutical composition is sterilized and contained in disposable single-dose containers for topical use in drop form, multiple vials in the form of a set of 30 vials, 60 vials and so on can be packaged in a tray with a lid, for example, a polypropylene tray with an aluminum peelable lid. The entire contents of each tray can be dispensed intact, and one vial or pack is used each time and immediately discarded after each use. For example, plastic ampules or vials or containers can be manufactured using blow-fill-seal (BFS) technology. The BFS processes may involve plastic extrusion, molding, aseptic filling, and hermetic sealing in one sequential operation and those processes are known in the art.

In a preferred embodiment, the dosage form of the invention is eye drops of oil-in-water emulsions, eye drop solutions containing the active ingredient brimonidine or a salt thereof solutions. Eye drops preferably contain, according to the invention, aqueous or oily suspensions of the active ingredient in pharmaceutically acceptable carriers and/or excipients. It is preferred in this connection for the particle size of the active ingredient employed to be less than 0.22 μm.

An example of various components (w/w) of a topical ophthalmic liquid formulation useful for treating an eye disorder (e.g., dry eye syndrome or MGD) in a human patient is as follows: brimonidine tartartrate in the amount of 0.01% to 0.2% by weight, preferably about 0.075%; 5 mM phosphate (combination of dibasic and monobasic) buffer of pH 7.4-8.0, preferably about 8.0 so as to make brimonidine more non-ionic beyond it's pKa of 7.8; a tonicity agent including mannitol of up to 5% by weight (in the range of 2-5% by weight); sodium EDTA in the amount of about 0.02% or less by weight, a small amount of thickening agents such as sodium carboxy methyl cellulose, HPMC or sodium hyaluronate. This formulation can be prepared by first preparing phosphate buffer with pH stabilized, for example, at 7.8-8.0 and then dissolving brimonidine tartrate in it by mixing thoroughly. Then, the remaining excipients are added and mixed thoroughly into solution. Final solution is sterile filtered using 0.22 micron filter and filled into single dose disposable tubes using, for example, BFS.

An example of a topical ophthalmic oil-in-water emulsion with its various components (w/w) useful for treating an eye disorder is as follows: brimonidine tartartrate in the amount of 0.02% to 0.2% by weight, preferably about 0.075%; surfactant such as Polysorbate 80 at about 0.02%-2% by weight or poloxamer/tyloxapol at about 0.1% and 0.25% by weight; carbomer copolymer (type A or type B) about 0.05% by weight; tonicity agent (glycerine or includes glycerine about 2.2% by weight; phosphate (combination of dibasic and monobasic) buffer of pH 7.4-8.0, preferably about 8.0 so as to make brimonidine more non-ionic beyond it's pKa of 7.8; sodium EDTA in the amount of about 0.02% or less by weight; an oil (e.g., castor oil) in the amount of about 1.25% by weight. Alternatively, the oil for the oil phase is a medium chain triglyceride in the range from 0.5-4%, preferably at about 2%. To prepare this formulation, all water soluble components except for brimonidine can be added and heated (about 60-70° C.) to make water the phase with buffer. Oil phase, the oil (e.g., castor oil) is heated to about 60-70° C. and brimonidine tartrate is dissolved or dispersed in it. Coarse emulsion is formed by rapid addition of oil into water phase followed by high shear mixing. Final emulsion is obtained by high pressure homogenization in a suitable equipment such as microfluidizer using several continuous cycles to obtain droplet size of less than 200 nm. The final emulsion is sterilized via 0.22 micron filter. Alternatively, sterilization can also be done by autoclaving at about 121° C. for 20 min. The sterilized emulsion is filled into single dose disposable tubes by BFS technology or the like.

Another example of a topical ophthalmic oil-in-water emulsion with its various components (w/w) useful for treating an eye disorder (e.g., dry eye syndrome or MGD) is as follows: it contains colloid particles with an average particle size of equal to or less than 0.2 μm and greater than 0.02 μm and has an oily core surrounded by an interfacial film. The size population distribution of the colloidal particles may be monomodal. The emulsion contains anywhere from 0.05% to 0.2% (e.g., 0.075%) alpha 2 adrenergic receptor agonist (e.g., brimonidine or a salt thereof) in weight to the total weight (w/w) of the emulsion, 0.5 to 4% w/w (e.g., 2% w/w) medium-chain triglycerides, 0.02% w/w benzalkonium chloride or no benzalkonium for single dose sterile containers, and surfactants. The surfactants, for example, consist of a mixture of tyloxapol in an amount of 0.3% w/w and poloxamer in an amount of 0.1% w/w. The ophthalmic oil-in-water emulsion can include one or more oils selected from olive, soy, corn, mineral, cottonseed, safflower and sesame. The emulsion does not contain substances capable of generating a negative charge and/or phospholipids. The ophthalmic oil-in-water emulsion can be used for treating a dry eye syndrome or MGD.

Yet another example of a topical ophthalmic oil-in-water emulsion with its various components (w/w) useful for treating an eye disorder is as follows: It contains an alpha 2 adrenergic receptor agonist in an amount of about 0.05%; polysorbate 80 (e.g. about 1.0% by weight); acrylate/C10-30 alkyl acrylate cross-polymer (about 0.05% by weight); water q.s.; and castor oil in an amount of about 1.25% by weight. The alpha 2 adrenergic receptor agonist is the only active agent present in the topical ophthalmic emulsion but contains a tonicity agent or a demulcent component (e.g., glycerine, which can be in an amount of about 2.2% by weight), a buffer. The pH of this topical ophthalmic emulsion may be in the range of about 7.4 to about 8.0. The topical ophthalmic emulsion is therapeutically effective in increasing tear production.

Yet another example of a topical ophthalmic oil-in-water emulsion with its various components (w/w) useful for treating an eye disorder is as follows: It contains an alpha 2 adrenergic receptor agonist brimonidine tartrate in an amount of about 0.2% (preferred 0.075%); polysorbate 80 (e.g. about 4% by weight); glycerin about 2.2%; carbomer copolymer type B (allyl pentaerythritol crosslinked) about 0.05% or the carbomer; sodium acetate 0.05%; boric acid about 0.1%; sodium ethylene diamine tetra acetic acid about 0.02%; sorbic acid about 0.1%; castor oil in an amount of about 5%; water q.s. to 20 ml (20 gms), preferably as part of a suitable buffer (boric acid/sodium acetate buffer can be substituted with mono/dibasic phosphate buffer) for this and other non-limiting examples described herein; and sodium hydroxide (0.1 N) q.s. to make pH 7.4-8.0; and water q.s. to 20 ml (20 gms). The topical ophthalmic emulsion is therapeutically effective for treating eye disorders.

Yet another example of a topical ophthalmic oil-in-water emulsion with its various components (w/w) is as follows: It contains brimonidine tartrate in an amount ranging from about 0.01% to about 0.5%, preferably in an amount of about 0.075%; carbomer homopolymer type B in an amount ranging from about 0.2 to about 0.6%, preferably in an amount of about 0.4% or about 0.25%, and/or carbomer homopolymer type C in an amount ranging from about 0.4 to about 5% preferably in an amount of about 4% or about 2.5%, and/or polycarbophil in an amount ranging from about 0.2% to about 0.5% preferably in an amount of about 0.4% or about 0.2%; glycerin in an amount ranging from about 0.5% to about 1% preferably in an amount of about 0.9%; benzalkonium chloride in an amount ranging from about 0.003% to about 0.01% preferably in an amount of about 0.007%; edetate sodium in an amount ranging from about 0.03% to about 0.07% preferably in an amount of about 0.05%; sodium chloride in an amount of up to about 0.09%, preferably in an amount of about 0.06% or q.s. to isotonicity, or mannitol q.s. to isotonicity, or without isotonicity adjustors sodium chloride and mannitol; propylene glycol in an amount ranging from about 0.3% to about 0.6% preferably in an amount of about 0.5%; water q.s., to 100 gms and sodium hydroxide or hydrochloric acid q.s., to adjust pH to 7.8. The topical ophthalmic emulsion is therapeutically effective for treating eye disorders. Although preservatives such as benzalkonium chloride can be used in the formulations of the present invention as described in the non-limiting examples, it is preferred that the formulations are preservative-free.

An example of a topical ophthalmic formulation with its various components (w/w) with a gel base useful for treating an eye disorder is as follows: The formulation contains an alpha 2 adrenergic receptor agonist and a hydrogel. The hydrogel can be hyaluronic acid, hydroxypropyl cellulose, hydroxypropylmethyl cellulose, hydroxyethylcellulose, polyvinyl pyrolidone, carboxymethylcellulose hydroxyethyl cellulose or polyvinylpyrrolidone.

These examples of topical ophthalmic compositions are intended to illustrate, but not limit, the present invention, are as described herein.

This invention also relates to a sealed package in which are sealed one or more pre-packaged disposable applicator sticks. The applicator sticks comprise an elongated handle portion and an absorbent applicator head portion containing a controlled amount of a composition comprising an alpha 2 adrenergic agonist (representative alpha 2 adrenergic agonists having described elsewhere herein) and an elongated handle portion. Thus, an embodiment of the medicinal applicator sticks containing an absorbent head portion and an elongated handle portion where a controlled amount of a composition comprising analpha 2 adrenergic agonist is absorbed in or adhered to the head portion is provided. The applicator sticks are disposable. Such disposable applicator sticks are commercially available. The disposable applicator stick(s) are removed from the sealed package by a clinician and used to apply a therapeutically effective amount of an alpha 2 adrenergic agonist directly to the margins of the eyelids of a subject in need of treatment for Meibomian gland dysfunction.

Compositions suitable for application using the applicator stick of the invention include liquid compositions for absorption by the absorbent head portion of the applicator stick or ointments adhered to the absorbent head portion of the applicator stick; typical liquid compositions are aqueous solutions of the alpha 2 adrenergic agonist and ointments are typically suspension of the alpha 2 adrenergic agonist in mineral oil or petrolatum jelly.

With respect to the medicinal applicator aspect of the invention, the term "controlled amount of a composition" refers to a predetermined amount of the composition comprising the alpha 2 adrenergic agonist that is absorbed in or adhered to the absorbent head of the applicator stick. The controlled amount can be readily determined by routine experimentation based on the characteristics of the composition and the absorbent head portion material(s). For example, in the case of a liquid composition, the predetermined amount is the amount of the liquid composition whereby the absorbent head portion of the applicator stick is not supersaturated but is just or almost fully saturated therewith. This avoids the problem of the liquid composition pooling in the package upon storage or running down the stick in the event the package is tilted.

The liquid absorbent applicator head portion of the applicator stick typically comprises absorbent fibers fixed to one end of the applicator stick. The absorbent fibers may be made of any naturally-occurring or synthetic fibers capable of absorbing the controlled amount of the liquid composition and then releasing the liquid composition in a controlled fashion upon contact with the subject's eyelid margin. In certain embodiments, the absorbent fibers comprise woven or unwoven cotton fibers. In other embodiments the absorbent fibers may comprise an absorbent foam such as polyurethane foam. The absorbent fibers may be adhesively attached to the end of the stick. The sticks may be manufactured from any material conventionally used for this purpose including wood, paper, plastic, and the like. In an embodiment, the applicator sticks are commercially-available cotton-tipped swabs for applying liquid-type materials.

Packaging systems for disposable applicator sticks are known in the art. In an embodiment, one or more applicator sticks according to the invention may be sealed in a pouch composed of a suitable flexible material (e.g. foil). Thus, an embodiment of the medicinal applicator aspect is a combination medicinal applicator and sealed package assembly therefor. The combination has at least one applicator having a liquid absorbent head portion and an elongated handle portion and a sealed package enclosing said at least one applicator.

Generally, in this aspect, a controlled amount of a composition containing an alpha 2 adrenergic agonist (e.g., an aqueous solution of brimonidine or a suspension of brimonidine in mineral oil or petrolatum jelly) is absorbed in or adhered to the head portion. The liquid composition contains about 0.001 to about 5 mg/ml brimonidine or brimonidine and, optionally, corticosteroids (e.g., methylprednisone) CRGP receptor antigonists or anti-CGRP receptor monoclonal antibodies, adrenomedullin inhibitors, serotonin inhibitors, cathelicidin inhibitors, or neuropeptides.

In another embodiment, the applicator sticks may be packaged in a rigid tray made of molded synthetic plastic material, the tray comprising a tray-forming body with a depression so that external compression forces on the applicator heads will not squeeze the liquid therefrom. In another embodiment, the rigid tray may have severable sections, each containing one or more applicator sticks for easy removal of the desired number of applicators. A flexible, gas impermeable cover sheet that is releasably but sealingly secured over the rigid tray(s) provides a gas-tight seal for the tray or tray sections involved and completes the sealing of the well-forming depression. The cover preferably comprises an upper layer made of a paper-like material and upon the outer face of which is printed information identifying the type of applicator involved and the medicinal material applied to the head portion thereof, and a trademark or logo identifying the manufacturer of the product.

In another embodiment, the package includes a tray-like body providing a depressed well and support ledge-forming portions shaped and arranged to cooperate respectively with the head and handle the applicator sticks so as to locate the head portions thereof below the handles and in head protecting wells, and with the portions of the handles to be grasped inclining and/or spaced upwardly so as to be out of contact with any bottom surfaces of the tray. In such case, the swabs or applicator sticks can be more conveniently grasped. The package is completed by a flexible, gas-impervious, cover sheet as described above.

The applicator of the present invention has its most important applications in two basically different forms of packages. In one form, each of the swabs or applicator sticks is sealed within a separable section of the tray-like body of the package. In the other form, the tray-like body of the package is a non-separable body and supports a number of swabs or applicator sticks either in a single compartment, whereupon removal of a single non-severable cover sheet therefrom all swabs or applicator sticks are simultaneously visible and preferably graspable at one time, or in separate compartments where each can be exposed separately as a severable portion of an overlying cover sheet is peeled from the tops of the package. The applicator head portion of the applicator sticks of the invention contain a controlled amount of a liquid composition comprising an alpha 2 adrenergic agonist.

In another aspect, the invention relates to methods of treating a subject or human patient suffering from an eye disorder by administering to the to the eye of the human patient an ophthalmological pharmaceutical formulation having a therapeutically effective amount of one more alpha 2 adrenergic agonists or a pharmaceutically acceptable salts thereof. The alpha-2-adrenergic agonist or mixtures thereof is present in an amount effective to provide a desired therapeutic benefit to a patient suffering from an eye disorder to whom the composition is administered. The therapeutically effective amount should be sufficient to realize relief from the eye disorder after the treatment.

In one embodiment, the alpha-2-adrenergic agonist is or includes brimonidine or a pharmaceutically acceptable salt thereof. The eye of a subject or human patient can be the entire eye structure or a tissue or gland in or around the eye such as the ocular tissue, eyelids, margin of the eyelid of the subject, ocular surface, Meibomian gland and or lacrimal gland of the human patient. The ophthalmological pharmaceutical formulation is topically administrable and/or is administered in, on or around the eye. In an embodiment of the invention, the eye disorder is dry eye syndrome or MGD. The dry eye syndrome may be aqueous tear-deficient dry eye (ADDE) or evaporative dry eye (EDE) or consists of both ADDE and EDE (mixed mechanism dry eye). In one preferred embodiment, MGD is treated according to this invention by applying a therapeutically effective amount an alpha 2 adrenergic agonist directly to the margin of the subject's eyelid using an applicator as described herein. The liquid composition is applied on the skin of the lower and upper eyelid margins at the base of the eyelashes using sterile single use applicators. For applying on lower eyelid margin, pull the eyelid down and apply. For applying on upper eyelid margin close the eyelids and apply.

The actual dose of the active compounds of the present invention depends on the specific compound, and on the condition to be treated; the selection of the appropriate dose is well within the knowledge of the skilled artisan.

Additional objects, advantages, and novel features of this invention will become apparent to those skilled in the art upon examination of the following examples thereof, which are not intended to be limiting. In the Examples, procedures that are constructively reduced to practice are described in the present tense, and procedures that have been carried out in the laboratory are set forth in the past tense.

EXAMPLES

The following working examples further illustrate the present invention. The examples below are carried out using standard clinical procedures and techniques that are well known and routine to those of skill in the art, except where otherwise described in detail. The working examples are offered by way of illustration and not by way of limitation.

Example 1

Treatment of Mixed Dry Eye Disease (Severe Year Deficiency Meibomian Gland Dysfunction (MGD))

A patient with severe mixed dry eye disease (severe tear deficiency Meibomian gland dysfunction (MGD) was treated with brimonidine 0.15% aqueous solution twice a day to the eyelash and eyelid margin area of each eye. Presence of extensive conjunctival and eyelid margin redness were noted before applying brimonidine. A significant reduction in conjunctival and eyelid margin redness was noted 15 minutes after brimonidine application (photographs of the patient's eyes taken before and after treatment with brimonidine not shown). The patient reported that symptoms of ocular discomfort reduced after applying brimonidine.

Example 2

Treatment of Ocular GVHD Patients with Meibomian Gland Dysfunction

This working example is provided to demonstrate that the use of brimonidine tartrate ophthalmic solution) (ALPHAGAN® P) 0.15% improves comfort (provides relief) and reduces Meibomian gland dysfunction (MGD) in patients with chronic Ocular Graft-Versus-Host-Disease (oGVHD).

A total of 18 patients with chronic ocular GVHD (eyes n=36) were studied using subjective end points. All patients had eye lid margin telangiectasia, eye lid margin excoriation, keratinization and poor or no expression of Meibomian glad secretion upon digital pressure. One drop of brimonidine solution was instilled twice a day on the ocular surface of each eye and the patients were instructed to immediately gently close the eye lids. Eye drop solution that escaped over the eye lid/eye lashes was spread on the eye lid margin using their fingertip. Patients were followed for 6 months or more. On follow up visits patients were asked to assess their overall change in comfort and MGD signs (redness of eye lid margin) from baseline. This Subjective Global Assessment (SGA) was performed as follows: Question (to patient): compared to before using brimonidine and now, how is your overall ocular comfort and eye lid margin/ocular redness? The responses were categorized on a five point scale as follows: Much worse, Worse, About the same, Improved and Much improved. At each visit, the physician (Sandeep Jain, MD) used his clinical evaluation (all signs and symptoms taken together) to provide a global assessment of the patients' change in MGD symptoms and signs. The Clinical Global Impression (CGI) responses were categorized on a seven point scale as follows: Marked worsening, Moderate worsening, Minimal worsening, Unchanged, Minimal improvement, Moderate improvement and Marked improvement.

Relevance of CGI (SGA) score to clinical end point in mean OSDI is the primary efficacy endpoint. In the Restasis Review of Efficacy and Safety vs Tears in the Relief of Dry Eye (RESTORE) study, minimal clinically important difference (MCID) was determined for the Ocular Surface Disease Index (a 12-item patient-reported outcome questionnaire designed to quantify ocular disability due to dry eye disease) (PMID: 20065224). A clinician global impression (CGI) and a subject global assessment (SGA) served as anchors to estimate the MCID for the overall OSDI score (range, 0-100). The overall OSDI score defined the ocular surface as normal (0-12 points) or as having mild (13-22 points), moderate (23-32 points), or severe (33-100 points) disease. The CGI and SGA correlated with the OSDI score change for all OSDI categories.

The mean (±SD) SGA was 4.4±0.69 suggesting that most patients reported subjective benefit from Brimonidine use. No patients reported worsening of symptoms or signs. Of the tested patients, 11% patients (n=2) did not report any change. 33% patients (n=6) reported improvement where as 55% patients (n=10) reported much improvement. The mean (±SD) CGI was 6.2±0.88 suggesting that most patients had clinical benefit from Brimonidine use. No patients had clinically worsened. 83% patients (n=15) had moderate to marked improvements in CGI. The eye drops were easily tolerated. The subjective beneficial effects reported were: reduced redness of eye lid margin and ocular surface, less need for concomitant artificial tear eye drops, less eye lid discomfort and easier opening of eyes in the morning. The clinical beneficial effect noted were: reduced eye lid margin telangiectasia, reduced eye lid margin excoriation and improved expression of Meibomian glad secretion upon digital pressure.

Thus, it has been demonstrated that the use of brimonidine to treat Meibomian gland dysfunction in ocular GVHD patients led to a beneficial effect in approximately 90% of the patients tested without significant side effects.

Example 3

Treatment of Patient(s) Diagnosed as Suffering from Sjogren Dry Eye Syndrome The patient was a 52-year-old female with documented history of Sjogren's syndrome. The prior treatment history was that the patient received steroid eye drops, bandage contact lens, systemic doxycycline, evoxac and extensive lubrication of the ocular surface. The patient had little improvement in signs and symptoms even after such an aggressive treatment. After a period of time, the patient underwent pre-treatment examination followed by treatment according to the invention herein. The patient showed severe symptoms of ocular discomfort, severe tear deficiency (Schirmer I of 4 mm in the right eye and 3 mm in the left eye), extensive ocular surface disease with 3+ corneal rose bengal staining in both eyes and presence of Meibomian gland dysfunction (MGD) in both eyes. The patient was treated with brimonidine 0.15% twice a day in both eyes. The patient was instructed to instil brimonidine on the eye surface and close the eye lids to spread excess drug onto eye lid margins of both eyes. The patient has reported improvement in symptoms and redness with brimonidine use.

Example 4

Treatment of Patient(s) Diagnosed as Suffering from Non-Sjogren Dry Eye Syndrome (MGD Not Due to Ocular GVHD)

The patient treated was a 59-year-old female with persistent complains of redness, irritation, burning and stinging in both eyes. Pre-treatment examination revealed normal aqueous tear production (Schirmer I of 16mm in the right eye and 13 in the left eye). Significant amount of lid margin telangiectasia was present along with Meibomian gland dropout and poor flow of oil on digital pressure. Patient did not have any autoimmune disorder. A diagnosis of Meibomian gland dysfunction (MGD) was made. The patient had little improvement in signs and symptoms following aggressive treatment that included steroid eye drops and systemic doxycycline pills. To demonstrate efficacy according to the invention herein, the patient was subject to brimonidine 0.15% twice a day. The patient applied brimonidine eye drops to both eyes and spread them on upper and lower lids of both eyes. On the most recent follow up the patient reported reduction in symptoms of dryness and burning and reduction in redness of both eyes with continued use of brimonidine. No side effects were reported and the drops were tolerated well. Patient wishes to continue using brimonidine.

Example 5

Treatment of Patients Diagnosed as Suffering from Evaporative Dry Eye (EDE)—Attributable to LASIK Refractive Surgery The patient treated was a 55-year-old female with severe symptoms of ocular discomfort. The patient had undergone LASIK refractive surgery in both eyes. The prior treatment history was that the patient was on doxycycline pills, warm compresses, erythromycin ointment and intermittently on steroid eye drops. The patient had little improvement in signs and symptoms. The examination of the patient, prior to the treatment according to the invention herein, revealed borderline tear deficiency (Schirmer I of 10 mm in the right eye and 11 mm in the left eye), mild corneal fluorescein staining and reduced corneal sensation in both eyes. Significant eye lid margin telangiectasia and Meibomian gland dysfunction (MGD) was seen in both eyes. To demonstrate efficacy according to the invention herein, brimonidine eye drops 0.15% were administered in both eyes. The patient instilled the eye drops on the surface of the eye and spread the excess eye drops to both eye lid margins. On the most recent follow up, the patient reported that symptoms improved 90% since starting brimonidine and wishes to continue using these eye drops.

The foregoing discussion of the invention has been presented for purposes of illustration and description. The foregoing is not intended to limit the invention to the form or forms disclosed herein. Although the description of the invention has included description of one or more embodiments and certain variations and modifications, other variations and modifications are within the scope of the invention, e.g., as may be within the skill and knowledge of those in the art, after understanding the present disclosure. It is intended to obtain rights which include alternative embodiments to the extent permitted, including alternate, interchangeable and/or equivalent structures, functions, ranges or steps to those claimed, whether or not such alternate, interchangeable and/or equivalent structures, functions, ranges or steps are disclosed herein, and without intending to publicly dedicate any patentable subject matter. All references cited herein are incorporated by reference in their entirety.

What is claimed is:

1. A method of treating a patient suffering from a dry eye syndrome comprising administering to an eye of the patient in need of such a treatment an ophthalmological pharmaceutical formulation comprising an active ingredient for treatment of a dry eye syndrome, wherein said active ingredient consists essentially of a therapeutically effective amount of an alpha 2 adrenergic agonist or a pharmaceutically acceptable salt thereof to treat a dry eye syndrome in said patient, wherein said alpha 2 adrenergic agonist or a pharmaceutically acceptable salt thereof has a higher alpha 2A agonist activity compared to alpha 2B agonist activity.

2. The method of claim 1, wherein the alpha 2A agonist activity of said alpha 2 adrenergic agonist is at least about 10% greater than the alpha 2B agonist activity.

3. The method of claim 1, wherein the alpha 2 adrenergic agonist comprises brimonidine or a pharmaceutically acceptable salt thereof.

4. The method of claim 1, wherein the dry eye syndrome comprises Meibomian gland dysfunction (MGD).

5. The method of claim 1, wherein the dry eye syndrome is aqueous tear-deficient dry eye (ADDE).

6. The method of claim 5, wherein the ADDE is Sjogren dry eye syndrome, ocular Graft-Versus-Host-Disease (oGVHD) or non-Sjogren dry eye syndrome.

7. The method of claim 1, wherein the dry eye syndrome is evaporative dry eye (EDE).

8. The method of claim 1, wherein the dry eye syndrome is mixed mechanism dry eye consisting of aqueous tear-deficient dry eye (ADDE) and evaporative dry eye (EDE).

9. The method of claim 1, wherein the dry eye syndrome is a complication of LASIK refractive surgery or is attributable to one or more causes selected from the group consisting of: vitamin A deficiency, ocular surface disorders, allergy, aging, contact lens usage and medication usage and disorders of eyelid aperture.

10. The method of claim 1, wherein the ophthalmological pharmaceutical formulation is eye hydrogel comprising at least one pharmaceutically acceptable excipient selected from the group consisting of carbomer homopolymer type B, carbomer homopolymer type C, polycarbophil, hyaluronic acid, carboxymethylcellulose, hydroxyethyl cellulose, hydroxypropyl cellulose, hydroxypropylmethyl cellulose and polyvinylpyrrolidone.

11. The method of claim 1, wherein the ophthalmological pharmaceutical formulation is sterilized preservative-free formulation and contained in disposable single-dose containers for topical use.

12. The method of claim 1, wherein the alpha 2 adrenergic agonist is or includes brimonidine or a pharmaceutically acceptable salt thereof being present in an amount from about 0.5% to about 0.0001% in weight to the total weight (w/w) of said formulation.

13. The method of claim 12, wherein the alpha 2 adrenergic agonist is present in an amount not more than about 0.2% w/w.

14. The method of claim 12, wherein the alpha 2 adrenergic agonist is present in an amount ranging from about 0.2% to 0.05% w/w.

15. The method of claim 12, wherein the alpha 2 adrenergic agonist is present in an amount ranging from about 0.15% to about 0.07% w/w.

16. A method for treating Meibomian gland dysfunction (MGD) in a subject in need of such a treatment, said method comprising applying an ophthalmic solution having an active ingredient for treating MGD to each eye of the subject, wherein said active ingredient consists essentially of a therapeutically effective amount of an alpha 2 adrenergic agonist, and wherein said alpha 2 adrenergic agonist has a higher alpha 2A agonist activity compared to alpha 2B agonist activity.

17. The method of claim 16, wherein the eye comprises a tissue or gland in or around the eye selected from the group consisting of ocular tissue, margin of the subject's eyelid, ocular surface, Meibomian gland and lacrimal gland of the human patient.

18. The method of claim 17, wherein said alpha 2 adrenergic agonist is brimonidine or a salt thereof.

19. A method of treating a patient suffering from a dry eye syndrome, said method comprising administering to an eye of a patient in need of such a treatment an ophthalmological pharmaceutical formulation consisting essentially of a therapeutically effective amount of brimonidine or a pharmaceutically acceptable salt thereof and optionally a pharmaceutically acceptable excipient to treat a dry eye syndrome in said patient.

20. The method of claim 19, wherein the therapeutically effective amount is an amount ranging from about 0.15% to about 0.07% w/w.

21. The method of claim 19, wherein the therapeutically effective amount is about 0.15% w/w.

22. The method of claim 19, wherein the dry eye syndrome comprises Meibomian gland dysfunction (MGD), ocular Graft-Versus-Host-Disease (oGVHD), Sjogren dry eye syndrome or non-Sjogren dry eye syndrome or is a complication of LASIK refractive surgery.

23. An aqueous ophthalmic solution for treating a patient suffering from a dry eye syndrome, wherein said aqueous ophthalmic solution consists essentially of:
(a) a therapeutically effective amount of an alpha 2 adrenergic agonist, a pharmaceutically acceptable salt thereof or a combination thereof to treat a patient suffering from a dry eye syndrome, wherein said alpha 2 adrenergic agonist has a higher alpha 2A agonist activity compared to alpha 2B agonist activity;
(b) a pharmaceutically acceptable excipient; and
(c) water.

24. The aqueous ophthalmic solution of claim 23, wherein said pharmaceutically acceptable excipient is selected from the group consisting of:
a crosslinking agent,
a surfactant,
gum,
a resin,
a pH adjuster,
a stabilizer,
an antioxidant,
a preservative,
an ultraviolet absorbent,
a wetting agent, and
a combination thereof.

25. The aqueous ophthalmic solution of claim 24, wherein said pharmaceutically acceptable excipient comprises polysorbate 80, poloxamer, tylaxopol, carbomer, glycerin, sodium hydroxide, hydrochloric acid, or a combination thereof.

26. The aqueous ophthalmic solution of claim 23, wherein said alpha 2 adrenergic agonist comprises brimonidine, a pharmaceutically acceptable salt thereof or a combination thereof.

* * * * *